(12) United States Patent
Christenson et al.

(10) Patent No.: US 7,056,534 B2
(45) Date of Patent: *Jun. 6, 2006

(54) COATED POTASSIUM CHLORIDE GRANULES AND TABLETS

(75) Inventors: Bradley L. Christenson, Blaine, MN (US); Phillip W. Dritsas, Shorewood, MN (US)

(73) Assignee: Upsher-Smith Laboratories, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/921,789

(22) Filed: Aug. 19, 2004

(65) Prior Publication Data

US 2005/0079219 A1 Apr. 14, 2005

Related U.S. Application Data

(63) Continuation of application No. 10/076,892, filed on Feb. 14, 2002, now Pat. No. 6,780,437, which is a continuation-in-part of application No. 10/040,070, filed on Oct. 23, 2001, now abandoned.

(51) Int. Cl.
*A61K 9/16* (2006.01)

(52) U.S. Cl. ............ 424/490; 424/464; 424/474; 424/489; 424/494

(58) Field of Classification Search ............ 424/474, 424/679, 153–156, 464–468, 489–494
See application file for complete search history.

(56) References Cited

U.S. PATENT DOCUMENTS

| | | | |
|---|---|---|---|
| 3,873,588 A | 3/1975 | Osawa et al. | |
| 4,235,870 A | 11/1980 | Leslie | |
| 4,259,315 A | 3/1981 | Lippmann et al. | |
| 4,259,323 A | 3/1981 | Ranucci | |
| 4,340,582 A | 7/1982 | Kriesel et al. | |
| 4,352,791 A | 10/1982 | Zaffaroni et al. | |
| 4,519,801 A | 5/1985 | Edgren | |
| 4,555,399 A | 11/1985 | Hsiao | |
| 4,748,023 A | 5/1988 | Tamas et al. | |
| 4,863,743 A * | 9/1989 | Hsiao et al. | 424/476 |
| 5,035,898 A | 7/1991 | Chang et al. | |
| 5,397,574 A | 3/1995 | Chen | |
| 5,422,122 A * | 6/1995 | Powell | 424/465 |
| 5,505,962 A * | 4/1996 | Sparks | 424/473 |
| 5,651,984 A | 7/1997 | Powell | |
| 6,245,351 B1 | 6/2001 | Nara et al. | |

OTHER PUBLICATIONS

Ethocel Polymers Dow Chemical Brochure, pp. 1-24, Feb. 1998.
Parikh, "Fluid-Bed Processing in the 1990s", Atlantic Pharmaceutical Services, Inc., <www.apsoutsource.com/two.html.>, 7 pages.
Parikh, "Current Issues and Troubleshooting Fluid Bed Granulation", Atlantic Pharmaceutical Services, Inc., <www.apsoutsource.com/three.html.>, 5 pages.
Sietz, et al., "Tablet Coating", Chapter 12 from *The Theory and Practice of Industrial Pharmacy*, by Lachman et al., 3$^{rd}$ Edition, pp. 346-373.

* cited by examiner

*Primary Examiner*—Michael Hartley
*Assistant Examiner*—Micah-Paul Young
(74) *Attorney, Agent, or Firm*—Faegre & Benson LLP

(57) ABSTRACT

This invention provides extended release potassium chloride granules consisting essentially of potassium chloride crystals having a mesh size of about 20–60 mesh that are coated only with ethylcellulose. The granules may be compressed into tablets that disintegrate rapidly in an aqueous environment to provide uniform dissolution of the potassium chloride. Tablets containing about 10 to about 20 milliequivalents potassium may be formulated in accordance with the invention. Processes to produce extended release granules without using surfactants, processing aids or other coating aids are also provided by this invention. A method is further provided whereby a patient's supplemental potassium requirements are met by administering an appropriate combination of dosage units chosen from available dosage units containing different quantities of potassium.

12 Claims, No Drawings

COATED POTASSIUM CHLORIDE GRANULES AND TABLETS

RELATED APPLICATION

This application is a continuation of U.S. patent application Ser. No. 10/076,892 filed on Feb. 14, 2002 now U.S. Pat. No. 6,780,437, entitled "Coated Potassium Chloride Granules and Tablets"; which is a continuation-in-part of U.S. patent application Ser. No. 10/040,070, filed on Oct. 23, 2001 now abandoned, entitled "Coated Potassium Chloride Granules and Tablets." The disclosure of each of the foregoing is incorporated herein by reference in its entirety.

BACKGROUND

This invention generally provides coated potassium chloride granules that may be used to make extended release potassium chloride tablets. Specifically, the present invention provides ethylcellulose-coated crystals of potassium chloride that may be orally administered to a patient requiring potassium supplementation. The coated potassium chloride granules provide extended release of the potassium chloride in the gastrointestinal tract that results in substantially less irritation to the gastric mucosa.

The administration of many diuretics, commonly used to treat patients having hypertension, increases the excretion of both sodium and potassium. The acute administration of such diuretics to a patient normally causes no problems. However, chronic administration of diuretics to some patients can result in the depletion of potassium from the patient, a condition known as hypokalemia. Potassium depletion may be accompanied by a reduced tolerance to carbohydrates and a deficiency in glycogen deposition. Further, vasopressin-resistant polyuria is another complication. A deficit of potassium also appears to increase the renal synthesis of prostaglandins, which in turn can decrease the permeability to water of the distal nephron and produce a diabetes insipidus-like syndrome.

In order to avoid these complications, supplemental potassium administration is typically needed. When potassium is taken along with a normal diet it is slowly absorbed from the intestinal tract. Following potassium distribution and uptake by the cells, the kidneys excrete an appropriate amount to maintain a proper balance. As a consequence of a large volume of distribution and a rapid response of the kidney, the extracellular and intracellular concentrations of potassium are normally maintained within relatively narrow limits.

When potassium is administrated as a drug, the factors that govern the rate and extent of its distribution are of major importance. It is not possible to increase the total cellular content of potassium significantly above normal. However, it is very easy to raise the extracellular concentration excessively. It is the concentration of potassium in the extracellular fluid that determines life-threatening toxicity.

It is well known that large doses of potassium chloride taken orally can cause gastrointestinal irritation, purging, weakness and circulatory disturbances. Since potassium depletion can cause problems for the patient, a controlled or extended release formulation of potassium chloride that replenishes potassium in an acceptable manner without undesirable side effects is desired.

In an attempt to meet the need for suitable formulations that may be used as a potassium supplement, a number of different dosage formulations have been developed. U.S. Pat. No. 4,352,791 reports a composition of potassium and a therapeutically acceptable salicylate salt of salicylic acid. U.S. Pat. No. 4,340,582 reports an enteric coated tablet that may include potassium chloride. U.S. Pat. No. 4,259,323 reports a potassium chloride emulsion. U.S. Pat. No. 4,259,315 reports a controlled release potassium dosage from gelatin capsules that contain a mixture of ethylcellulose-encapsulated potassium chloride and a hydrophilic surfactant. Film-coated tablets containing potassium chloride in a wax matrix (non-enteric coated) are marketed as a slowly available potassium source. U.S. Pat. No. 4,235,870 reports a slow release pharmaceutical composition of a combination of higher aliphatic alcohols and hydrated hydroxyalkyl cellulose. U.S. Pat. No. 4,863,743 reports a controlled release potassium chloride tablet made of potassium chloride crystals coated with higher molecular weight (measured viscosity greater than 40 cP in toluene/ethanol) ethylcellulose and hydroxypropylcellulose. U.S. Pat. No. 5,397,574 reports controlled release potassium chloride micropellets coated with lower molecular weight (measured viscosity less than 10 cP in toluene/ethanol) ethylcellulose and a plasticizer.

SUMMARY OF THE INVENTION

This invention provides a potassium chloride granule that contains both crystals of potassium chloride and a thermoplastic cellulose ether that forms a coating on the crystals. No other agents, additives, surfactants, or coating and processing aids are used or included in the granule. In one embodiment of the invention the potassium chloride crystals have a size of about 20–60 mesh. In another embodiment the thermoplastic cellulose ether is ethylcellulose having a measured viscosity of about 20 cP.

This invention also includes an extended release tablet made of a plurality of the ethylcellulose-coated potassium chloride granules. The potassium chloride granules that are in the tablet are essentially free of surfactants or other processing additives and agents. The term "essentially free" indicates the absence of surfactants, additives, agents or coating and processing aids during the processing of the granules.

The invention also includes dosage units having different potencies, including 10 milliequivalents (mEq) potassium per unit, 15 mEq potassium per unit, and 20 mEq potassium per unit.

Further, the invention includes a process to produce ethylcellulose-coated potassium chloride granules comprising the steps of i) forming a fluidized bed of potassium chloride crystals at a dew point of about 10–20° C., ii) spraying the fluidized crystals with a mixture of only ethylcellulose, alcohol and water sufficient to coat the crystals, and iii) drying the coated crystals to remove the alcohol and water to provide ethylcellulose-coated potassium chloride granules.

The invention also provides a process for producing ethylcellulose-coated granules in which no additives are required during the spray-coating step for the control of static buildup in the fluid bed processor. The process comprises the steps of i) forming a fluidized bed of potassium chloride crystals, ii) spraying the fluidized crystals with a mixture consisting of ethylcellulose, alcohol, and sufficient water to control the buildup of static charge to enable substantially complete coating of the crystals, and iii) drying the coated crystals to remove the alcohol and water to provide ethylcellulose-coated potassium chloride granules.

Also provided by the present invention is a method for customizing a patient's supplemental potassium dosage regimen. The method comprises providing dosage units (such as, e.g., tablets) having different potencies, and then administering to the patient a suitable combination of dosage units to meet the patient's supplemental potassium requirements.

DETAILED DESCRIPTION OF THE INVENTION

The present invention provides an extended release potassium chloride tablet that includes ethylcellulose-coated potassium chloride crystals. No other surfactants or processing additives and agents are used in, or are part of, the coating.

In the practice of the present invention, one suitable method for coating potassium chloride is by fluid-bed processing. Static buildup is typically controlled in ordinary fluid-bed processing methods by means of a processing additive. One undesirable consequence of excessive static buildup is that particulate material may stick to the walls of the processing chamber, which can result in reduced yield or efficiency. The material sticking to the walls will be incompletely coated and may not be included with the final product, leading to decreased yield. Material clinging to the chamber walls also complicates cleanup between processing runs. An additional consequence of the presence of excessive static is an increased risk of explosion. An explosion can be triggered by static discharge in the fluid bed environment, due to the large amounts of fine dust present and, in some cases, the presence of organic solvent vapors.

Some common additives that are used to control static buildup include magnesium stearate, titanium dioxide, and talc as well as commercially available products sold under the trade names STAT-LES by Walter G. Legge Company, Inc., Peekskill, N.Y., and LAROSTAT by PPG/Mazer Chemicals, Gurnee, Ill. Nonionic surfactants have also been used as additives for static control. Suitable nonionic surfactants possess a hydrophilic-lipophilic balance (HLB) number in the range 4–15. Examples of suitable nonionic surfactants include sorbitan monooleate (SPAN 80, HLB 4.3), polysorbate 60 (TWEEN 60, HLB 14.9) and polysorbate 80 (TWEEN 80, HLB 15.0). The compositions and processes of the present invention do not require additives for static control.

Plasticizers are another class of processing additives that are commonly used in the manufacturing process. A plasticizer can be used to change the flexibility, tensile strength or adhesion properties of a polymeric film. When used in a pharmaceutical coating, a plasticizer can be used to improve or optimize the friability of a dosage unit or the dissolution profile of a delayed-release or extended-release dosage unit. Some common plasticizers that find use in pharmaceutical coating applications include dibutyl phthalate, diethyl phthalate, triethyl citrate, tributyl citrate, acetylated monoglyceride, acetyl tributyl citrate, dimethyl phthalate, benzyl benzoate, propylene glycol, butyl and glycol esters of fatty acids, low-molecular-weight polyethylene glycols, refined mineral oils, glycerin, oleic acid, organic acid esters, stearyl alcohol, castor oil, corn oil and camphor. The compositions and processes of the present invention do not utilize plasticizers as additives for the thermoplastic polymer coating.

The active ingredient of the tablet provided by the present invention is potassium chloride. Potassium chloride is administered to a patient in such a manner in order to prevent or relieve potassium depletion and to avoid side effects. The potassium chloride tablets of the present invention may be co-administered with a diuretic.

Potassium chloride occurs in nature as the mineral sylvine or sylvite. Various industrial preparations of potassium chloride also exist Further, there are numerous pharmaceutical potassium chloride preparations. Potassium chloride is a white crystal or crystalline powder having the following physical description: d 1.98; mp 773° C.; 1 gram dissolves in 2.8 ml water; 1.8 ml boiling water; 14 ml glycerol; about 250 ml ethyl alcohol; and is insoluble in ether and acetone.

In the present invention, potassium chloride crystals having a particle size distribution ranging from about 20–60 mesh are subjected to coating or encapsulation in ethylcellulose to produce coated potassium granules. The coated granules may subsequently be compressed into a tablet.

By providing a suitable coating weight of the ethylcellulose, a thermoplastic cellulose ether polymer film may be formed on the crystals that remains intact in the stomach (and afterwards) but which is permeable to gastric fluids. The gastric fluids dissolve and leach out the potassium chloride contained in the coated crystals.

The thermoplastic polymer coating of ethylcellulose on the crystals makes up about 17% of the total weight of granules. Lesser amounts of ethylcellulose in the coating may lead to or cause the formation of bare spots on the potassium chloride crystals during the compression step, leading to undesirably rapid release of the potassium chloride in the body after oral administration. Greater amounts of ethylcellulose, as the thermoplastic polymer coating, may cause the potassium chloride to be released too slowly to be completely absorbed by the patient. In one embodiment, potassium chloride is coated with ethylcellulose having a suitable molecular weight such as ethylcellulose designated as having a product viscosity of 20 and sold under the trademark ETHOCEL by Dow Chemical Company, Midland, Mich. The numerical designations for ethylcellulose generally correspond to the viscosity of the product, with a greater numerical designation indicating a greater measured viscosity and higher molecular weight. The 20 designation corresponds to a viscosity of about 18–22 cP as measured in a 5% by weight solution in an 80% toluene-20% ethanol solvent at 25° C. in an Ubbelohde viscometer. The ethoxyl content for ETHOCEL Standard 20 Premium cellulose ether is about 48–49.5%.

In an embodiment of the invention, the individual crystals of potassium chloride are coated with the appropriate materials to produce coated granules, which are mixed with acceptable compression aids and disintegrants and then compressed into tablets. The tablets are compressed in a manner so as to allow the tablets to disintegrate relatively quickly upon contact with an aqueous environment into the individual coated granules, i.e., disintegration takes place in a short period of time after oral administration.

The manufacturing process utilized in the present invention applies a controlled and uniform coating, permitting uniform dissolution. Accordingly, the rapid disintegration and controlled dissolution of the tablets into individual granules and the controlled dissolution of the granules permit the peristaltic motion of the gut to distribute the coated granules over a wide surface area. As a result, concentrated quantities of potassium chloride do not come in contact with the gastrointestinal mucosa, thus reducing the undesired side effect of gastric ulcers.

The importance of potassium supplement therapy has been well established. Physicians need products for the prevention of hypokalemia during chronic diuretic therapy. Compliance is essential for patients undergoing this type of therapy. Potassium chloride is normally provided in relatively large oral dosages in the range of 2 to 4 grams daily.

Because of the large amount of the potassium chloride which is provided to the patient, gastrointestinal irritation is common. This irritation can range from a slight discomfort to gastric ulcers. By including potassium chloride crystals in the granules in the manner indicated above and then compressing them in a conventional manner into tablets, the gastrointestinal irritation is alleviated or eliminated.

Dosages of supplementary potassium are measured in milliequivalents (mEq) of potassium per dosage unit. One mEq, which is equal to one millimole, is provided by approximately 39 milligrams of potassium, or approximately 75 milligrams of potassium chloride. The recommended dose for most patients is 40 mEq per day in divided doses. In accordance with currently approved labeling a single dose of 20 mEq (or 2 doses of 10 mEq) should be taken twice daily in order to obtain a daily dose of 40 mEq. With the formulation provided by the present invention, suitable tablets will include a dose of 20 mEq so that the recommended effective amount of potassium per single dose would not be altered. The daily dose is achieved with one tablet twice daily thus facilitating compliance due to less individual units per dose. Alternatively, other dosage units having 10 mEq or 15 mEq are included in the present invention and provide flexibility in establishing a regimen that meets a patient's needs.

In severe cases of hypokalemia, higher doses (60–80 mEq) of potassium may be required to reduce the loss of potassium during high dose diuretic therapy. In such cases, the physician would have available a safe higher-strength tablet where, in his judgment, he is treating a patient with a compliance problem.

The tablets produced by the present invention disintegrate into numerous sub-units when placed in water or placed on an aqueous food. After being disintegrated into the sub-units or micro-pellets the potassium chloride of the present invention can be more easily administered to children and geriatric patients who often have difficulty in swallowing large tablets. The tablets may include conventional compression aids such as microcrystalline cellulose and disintegrants such as croscarmellose sodium. In addition, other additives may be beneficial. For example, magnesium stearate or stearic acid could be added as lubricating agent, if necessary, to the compositions and methods of the present invention.

The following formulation is suitable in the practice of the present invention for providing a dosage unit in tablet form having a potency of 10 mEq: potassium chloride, 750 milligrams (75.3 wt.-%); ethylcellulose, 154.4 milligrams (15.5 wt.-%); microcrystalline cellulose, 86.7 milligrams (8.7 wt.-%); croscarmellose sodium, 5 milligrams (0.5 wt.-%).

The following formulation is suitable in the practice of the present invention for providing a dosage unit in the form of a tablet having a potency of 15 mEq: potassium chloride, 1125 milligrams (75.3 wt.-%); ethylcellulose, 231.6 milligrams (15.5 wt.-%); microcrystalline cellulose, 130 milligrams (8.7 wt.-%); croscarmellose sodium, 7.5 milligrams (0.5 wt.-%).

The following formulation is suitable in the practice of the present invention for providing a dosage unit in the form of a tablet having a potency of 20 mEq: potassium chloride, 1500 milligrams (75.3 wt.-%); ethylcellulose, 308.8 milligrams (15.5 wt.-%); microcrystalline cellulose, 173.4 milligrams (8.7 wt.-%); croscarmellose sodium, 10 milligrams (0.5 wt.-%).

The three exemplary formulations listed above for tablet-form dosage units having the specified potency may be processed as follows: The potassium chloride is coated with a solution of ethylcellulose, water and methyl alcohol using the fluidized bed process described below, to produce coated potassium chloride granules. The coating solution consists of 87.6 wt.-% methyl alcohol (NF grade), 2.1 wt.-% water (purified, USP grade) and 10.3 wt.-% ethylcellulose (ETHOCEL Standard 20 Premium). During the coating step, it is important to control the ratio of potassium chloride to ethylcellulose to achieve the desired end-result formulations given above. Using the coating solution indicated, to achieve the above-listed formulations the proper ratio (weight:weight) of coating solution to potassium chloride is 2.0:1. After coating, the potassium chloride granules are dried to remove all the water and methyl alcohol. The granules are then blended with microcrystalline cellulose and croscarmellose to achieve the desired end-result formulation, and the mixture is compressed into tablets using a rotary tablet press. Using the formulations and quantities indicated above, the proper ratio (weight:weight) of coated potassium chloride granules to microcrystalline cellulose (NF) is 10.4:1, and the proper ratio (weight:weight) of coated potassium chloride granules to croscarmellose sodium is 181:1.

The invention further includes a process to produce ethylcellulose-coated potassium chloride granules comprising the steps of i) forming a fluidized bed of potassium chloride crystals at a dew point of about 10–20° C., ii) spraying the fluidized crystals with a mixture of only ethylcellulose, alcohol and water sufficient to coat the crystals, and iii) drying the coated crystals to remove the alcohol and water to provide ethylcellulose-coated potassium chloride granules. The alcohol solvent can be any of the low-boiling $C_1$–$C_4$ alcohols, such as ethyl alcohol or isopropyl alcohol, and preferably methyl alcohol. A suitable ethylcellulose/water/alcohol mixture for the practice of this process is the 87.6 wt.-% methyl alcohol/2.1 wt.-% water/10.3 wt.-% ethylcellulose solution described above.

The invention also provides a process for producing ethylcellulose-coated granules in which no additives are required during the spray-coating step for the control of static buildup in the fluid bed processor. The process comprises the steps of i) forming a fluidized bed of potassium chloride crystals, ii) spraying the fluidized crystals with a mixture consisting of ethylcellulose, alcohol, and sufficient water to control the buildup of static charge to enable substantially complete coating of the crystals, and iii) drying the coated crystals to remove the alcohol and water to provide ethylcellulose-coated potassium chloride granules. A water content of approximately 0.5 to 2% by weight has been found to be satisfactory for the control of static buildup in the fluid bed processor. Water content up to about 4% by weight was also found to be effective, but the additional increment of water provided no additional reduction in static buildup. The alcohol solvent can be any of the low-boiling $C_1$–$C_4$ alcohols, such as ethyl alcohol or isopropyl alcohol, and preferably methyl alcohol. A suitable ethylcellulose/water/alcohol mixture for the practice of this process is the 87.6 wt.-% methyl alcohol/2.1 wt.-% water/10.3 wt.-% ethylcellulose solution described above.

A method is provided by the present invention, whereby a patient's supplemental potassium requirements may be met by utilizing a customized dosage regimen. In the practice of this method, dosage units of different potencies are provided, and the patient's dosage regimen is determined by utilizing an appropriate combination of the dosage units to meet the patient's daily requirements of supplemental potassium. The dosage regimen is then administered to the patient. The various dosage units described herein are suitable for practice of this embodiment of the present invention.

By way of example, dosage units of 10 mEq, 15 mEq and 20 mEq potencies may be provided in the practice of this embodiment of the invention. Then, a patient requiring, for example, a daily supplemental dose of 30 mEq potassium may be administered by any of the following regimens: twice-daily administration of 15 mEq dosage units; thrice-daily administration of 10 mEq dosage units; daily administration of one 10 mEq dosage unit and one 20 mEq dosage unit.

Further, the method provides flexibility in meeting the needs of a patient whose daily requirement is, for example, 25 mEq, which is not readily accomplished when dosage units containing 10 mEq and 20 mEq are the only potencies available. A patient whose daily requirement is 25 mEq potassium per day may be administered the following regimen: daily administration of one 15 mEq dosage unit and daily administration of one 10 mEq dosage unit.

The present invention is further described in the following non-limiting example.

COMPARATIVE EXAMPLE

Dosage proportional 10 mEq and 20 mEq tablets were compressed from a blend of materials listed in Table 1 which includes ethylcellulose-coated potassium chloride granules. The Tablet A formula for the coated potassium chloride granules included sorbitan monooleate (SORBITAN) added to the coating solution. The SORBITAN was added with small amounts of purified water to the coating solution during the coating process, to reduce static buildup. The added purified water was removed during the coating process, but the nonvolatile SORBITAN was retained in the polymeric coating. The Tablet B formula for the coated potassium chloride granules did not include SORBITAN.

TABLE 1

| Ingredient | Tablet A | | Tablet B | | |
|---|---|---|---|---|---|
| | 10 mEq (wt. -%) | 20 mEq (wt. - %) | 10 mEq (wt. - %) | 15 mEq (wt. - %) | 20 mEq (wt. -%) |
| Sorbitan Monooleate | 0.4 | 0.4 | -0- | -0- | -0- |
| Potassium Chloride | 75.0 | 75.0 | 75.3 | 75.3 | 75.3 |
| Ethylcellulose | 15.4 | 15.4 | 15.5 | 15.5 | 15.5 |
| Microcrystalline Cellulose | 8.7 | 8.7 | 8.7 | 8.7 | 8.7 |
| Croscarmellose Sodium | 0.5 | 0.5 | 0.5 | 0.5 | 0.5 |
| Total mg/tablet | 1,000 | 2,000 | 996 | 1,494 | 1,992 |

A blend of the listed materials used to form a 400 kg lot was compressed into both 10 mEq and 20 mEq tablets to provide Tablet A in two dosages. The dissolution profiles for the two tablets are listed in Table 2. The dissolution specification for the 1, 2, 6 and 12 hour dissolution test points are: for one hour not less than 10% not more than 30%; for two hours not less than 20% not more than 60%; for six hours not less than 50% not more than 90%; and for twelve hours not less than 85%.

TABLE 2

| Tablet A | 1 Hour | 2 Hour | 4 Hour | 6 Hour | 8 Hour | 12 Hour |
|---|---|---|---|---|---|---|
| 10 mEq with SORBITAN | 19% | 34% | 61% | 79% | 91% | 100% |
| 20 mEq with SORBITAN | 18% | 31% | 56% | 76% | 91% | 100% |

A blend of materials listed in Table 1 was used to form 400 kg lot was compressed into 10 mEq, 15 mEq and 20 mEq tablets to provide Tablet B in three dosages. By increasing the amount of purified water added to the coating solution by about 2% by weight, the SORBITAN was removed from the coating solution while still controlling the amount of static charge present in a Wurster Coater during the coating procedure. The dissolution profiles for the three tablets are listed in Table 3.

TABLE 3

| Tablet B | 1 Hour | 2 Hour | 4 Hour | 6 Hour | 8 Hour | 12 Hour |
|---|---|---|---|---|---|---|
| 10 mEq | 24% | 42% | 67% | 86% | 98% | 104% |
| 15 mEq | 23% | 41% | 68% | 87% | 97% | 101% |
| 20 mEq | 24% | 39% | 64% | 87% | 97% | 104% |

The revised Tablet B 10 mEq, 15 mEq and 20 mEq tablets meet the same dissolution specification used for the Tablet A 10 mEq and 20 mEq tablets. The data also indicates that the extended release properties of both sets of tablets are substantially the same, even though the Tablet B set does not include SORBITAN.

Both Tablet A dosages and Tablet B dosages were made using known processes. Briefly, a solution of ethylcellulose in methyl alcohol and water (with and without SORBITAN, respectively) was sprayed onto potassium chloride crystals in a 32-inch Wurster coater. The process parameters used for the coater are listed in Table 4.

TABLE 4

| Bottom Plate Configuration | G upbed plate, B downbed plate |
|---|---|
| Partition Height | 25 mm |
| Spray Nozzle Size | 2.2 mm |
| Spray Rate/Nozzle | 600–1000 g/min |
| Atomization Air Volume | 50–60 cfm |
| Product Temperature | 45–60° C. |
| Process Air Volume | 2700–3700 cfm |

After coating, the potassium chloride granules were then dried and blended with microcrystalline cellulose and croscarmellose sodium and compressed into tablets using a rotary tablet press.

What is claimed is:

1. A method for customizing a patient's supplemental potassium dosage requirement of about 25–80 mEq potassium comprising:
   i) providing at least two individual pharmaceutical dosage units from the group consisting of a first individual dosage unit containing about 10 mEq potassium, a second individual dosage unit containing about 15 mEq potassium, and a third individual dosage unit containing about 20 mEq potassium; and
   ii) administering a suitable combination of the 10 mEq, 15 mEq, and/or 20 mEq individual dosage units that in single or multiple administration meets the patient's supplemental potassium requirement, wherein each of the dosage units is an extended-release tablet comprising a plurality of granules consisting of potassium chloride crystals between about 20–60 mesh and having a continuous coating consisting of a single thermoplastic cellulose ether.

2. A method according to claim 1, wherein the administering is done occasionally.

3. A method according to claim 1, wherein the administering is done as a daily regimen.

4. A method according to claim 1, wherein the thermoplastic cellulose ether is ethylcellulose.

5. A method according to claim 1, wherein the single or multiple administration provides a dosage in the range of about 25–45 mEq potassium.

6. A method according to claim 1, wherein the patient's supplemental potassium dosage requirement is about 30 mEq potassium or about 45 mEq potassium, and individual pharmaceutical dosage units containing about 15 mEq potassium are provided.

7. A method for customizing a patient's supplemental potassium dosage requirement of about 25–80 mEq potassium comprising:
   i) providing at least two individual pharmaceutical dosage units from the group consisting of a first individual dosage unit containing about 10 mEq potassium, a second individual dosage unit containing about 15 mEq potassium, and a third individual dosage unit containing about 20 mEq potassium; and
   ii) administering a suitable combination of the 10 mEq, 15 mEq, and/or 20 mEq individual dosage units that in single or multiple administration meets the patient's supplemental potassium requirement, wherein each of the dosage units is an extended-release tablet comprising a plurality of granules consisting of potassium chloride crystals essentially free of surfactants or processing aids and agents, between about 20–60 mesh, and having a continuous coating consisting of a single thermoplastic cellulose ether.

8. A method according to claim 7, wherein the administering is done occasionally.

9. A method according to claim 7, wherein the administering is done as a daily regimen.

10. A method according to claim 7, wherein the thermoplastic cellulose ether is ethylcellulose.

11. A method according to claim 7, wherein the single or multiple administration provides a dosage in the range of about 25–45 mEq potassium.

12. A method according to claim 7, wherein the patient's supplemental potassium dosage requirement is about 30 mEq potassium or about 45 mEq potassium, and individual pharmaceutical dosage units containing about 15 mEq potassium are provided.

* * * * *